United States Patent
Quirno et al.

(10) Patent No.: US 8,252,001 B2
(45) Date of Patent: Aug. 28, 2012

(54) APPARATUS AND METHODS FOR INTER-OPERATIVE VERIFICATION OF APPROPRIATE SPINAL PROSTHESIS SIZE AND PLACEMENT

(75) Inventors: Martin Quirno, New York, NY (US);
Natalia J. Schmidt, Howell, NJ (US);
Ashley Steimle, Toms River, NJ (US);
Trupti Karkar, Dumont, NJ (US);
Jacqueline K. C. Hilt, Clifton, NJ (US);
Vikki Hazelwood, Wayne, NJ (US);
Antonio Valdevit, Effort, PA (US)

(73) Assignee: Q-Spine LLC, New York, NY (US)

( * ) Notice: Subject to any disclaimer, the term of this patent is extended or adjusted under 35 U.S.C. 154(b) by 461 days.

(21) Appl. No.: 12/549,315

(22) Filed: Aug. 27, 2009

(65) Prior Publication Data
US 2010/0179558 A1 Jul. 15, 2010

Related U.S. Application Data

(60) Provisional application No. 61/092,559, filed on Aug. 28, 2008.

(51) Int. Cl.
*A61B 17/58* (2006.01)
*A61B 17/60* (2006.01)
*A61F 2/00* (2006.01)
(52) U.S. Cl. .................................................. 606/102
(58) Field of Classification Search ............ 606/57, 606/246, 279, 282, 90, 99, 102, 104, 105, 606/86 A, 914, 916
See application file for complete search history.

(56) References Cited

U.S. PATENT DOCUMENTS

| | | | |
|---|---|---|---|
| 3,872,590 A | 3/1975 | Hill | |
| 4,621,250 A | 11/1986 | Echasseriau et al. | |
| 6,227,081 B1 | 5/2001 | Bally et al. | |
| 6,261,296 B1 | 7/2001 | Aebi et al. | |
| 6,551,316 B1 | 4/2003 | Rinner et al. | |
| 6,984,993 B2 | 1/2006 | Ariav | |
| 7,189,234 B2 | 3/2007 | Zucherman et al. | |
| 2002/0116009 A1* | 8/2002 | Fraser et al. | 606/99 |
| 2003/0226272 A1 | 12/2003 | Finefield | |
| 2004/0059261 A1 | 3/2004 | Grinberg | |
| 2004/0116835 A1 | 6/2004 | Holmes | |
| 2004/0133132 A1 | 7/2004 | Chappuis | |
| 2004/0249388 A1 | 12/2004 | Michelson | |

(Continued)

OTHER PUBLICATIONS

ProDisc-L Total Disc Replacement, Technique Guide, Synthes Spine (Sep. 2006).

(Continued)

*Primary Examiner* — Kevin T Truong
*Assistant Examiner* — Sameh Boles
(74) *Attorney, Agent, or Firm* — Weitzman Law Office, LLC (57) ABSTRACT

A distractor and measuring device includes a first handle operatively connected to a first paddle and a second handle operatively connected to a second paddle. The first and second handles are pivotally connected to one another such that movement of the handles relative to one another causes the paddles to move relative to each other. At least one transducer is positioned on at least one of the first and second handles for measuring an amount of force applied during distraction. A measurement rod is pivotally connected to the device and is movable in a longitudinal direction relative to the first and second paddles. A potentiometer is operatively connected to the measurement rod to measure the angular orientation of the measurement rod.

23 Claims, 8 Drawing Sheets

U.S. PATENT DOCUMENTS

| | | |
|---|---|---|
| 2005/0021044 A1* | 1/2005 | Stone et al. .................. 606/102 |
| 2005/0080425 A1 | 4/2005 | Bhatnagar et al. |
| 2005/0159756 A1 | 7/2005 | Ray |
| 2005/0203532 A1 | 9/2005 | Ferguson et al. |
| 2006/0004380 A1 | 1/2006 | Didomenico et al. |
| 2006/0074431 A1 | 4/2006 | Sutton et al. |
| 2007/0209222 A1 | 9/2007 | Fischer et al. |
| 2007/0244488 A1* | 10/2007 | Metzger et al. ................ 606/90 |
| 2007/0260260 A1 | 11/2007 | Hahn et al. |
| 2008/0082169 A1 | 4/2008 | Gittings et al. |

OTHER PUBLICATIONS

Burt Yaszay, MD, et al., Effect of Intervertebral Disc Height on Postoperative Motion and Outcomes After ProDisc-L Lumbar Disc Replacement, SPINE, vol. 33, No. 5, pp. 508-512 (2008).

* cited by examiner

APPARATUS AND METHODS FOR INTER-OPERATIVE VERIFICATION OF APPROPRIATE SPINAL PROSTHESIS SIZE AND PLACEMENT

CROSS-REFERENCE TO RELATED APPLICATION

This application claims the benefit of U.S. Provisional Application No. 61/092,559, filed Aug. 28, 2008, the entire disclosure of which is incorporated herein by reference.

BACKGROUND

1. Field

This disclosure relates generally to apparatus and methods for use with spinal surgery and, more particularly, to apparatus and methods for precise spinal surgery disc placement.

2. Background

Chronic lower back pain caused by degenerative disc disease is one of the leading causes of disability in adults. Intervertebral disc degeneration can occur as part of the normal aging process in which the nucleus of the disc dehydrates, reducing the shock absorbing capability of the disc. Patients who fail to obtain adequate pain relief from non-surgical treatment (e.g., rest, pain medication, physical therapy, exercise, epidural steroid injections, chiropractic manipulation, ultrasound, massage, orthotics, etc.) may require spinal surgery to alleviate discogenic pain and disability.

One method of treating degenerative disc disease is spinal fusion or arthrodesis surgery in which the affected vertebrae are fused together using a bone graft. Another approach for treating degenerative disc disease is total disc replacement ("TDR") in which the pain-generating intervertebral disc is removed and a metallic artificial disc implant that allows motion is inserted into the intervertebral space between the adjacent vertebrae. The implanted spinal fusion cage or TDR implant (collectively referred to as "intervertebral implant") must be appropriately sized to restore the normal disc height at the affected vertebral segment, thereby reducing chronic discogenic pain, while maintaining or minimizing loss of range of motion in the affected vertebral segment.

It is estimated that approximately 3% of fusions and 3-8% of TDR procedures performed each year require revision. Some of these revisions are believed to be due to the misplacement and incorrect size selection of the intervertebral implant (e.g., artificial disc or fusion cage), which is based predominantly on the judgment of the surgeon at the time of the procedure.

Figure 1:
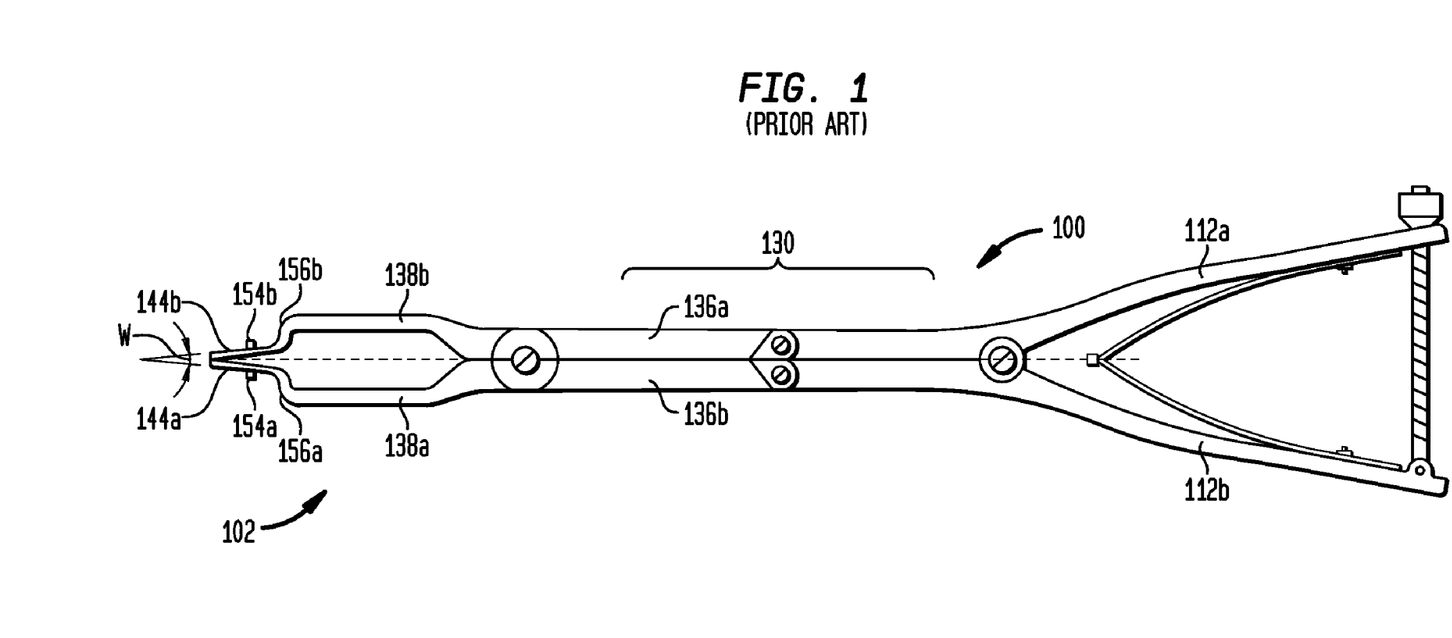
FIG. 1 is a side elevational view of a prior art distractor disclosed in the '296 patent.

Currently, there exist a variety of devices and methods for use in spinal surgery that are related to spinal disc space distractors. For instance, FIG. 1 shows a spinal disc space distractor that is depicted in U.S. Pat. No. 6,261,296 ("the '296 patent"). Devices such as those disclosed in the '296 patent provide grip and tightening mechanisms that are useful due to their mechanical advantages. Although the distractor device disclosed in the '296 patent is capable of opening up the disc (intervertebral) space, such conventional distractor devices do not provide the surgeon with the ability to accurately measure endplate length and disc height for the optimal selection, sizing and placement of the artificial disc, fusion cage or other intervertebral implant. Instead, the selection, sizing and placement of the artificial disc or fusion cage are based predominantly on the judgment of the surgeon at the time of the procedure.

Because conventional distractors lack measuring capabilities, discs may be distracted too much or too little, or the intervertebral implant may be placed in the wrong position. Incorrect selection, sizing and placement of the artificial disc or fusion cage may lead to many serious post-operative complications.

For instance, if the implant selected is too large for the intervertebral space, the implant could over-stuff the intervertebral space, which can reduce the patient's range of motion. Furthermore, if the surgery is a total disc replacement and the implant selected is too large for the space, the implant could create a fusion, instead of preserving the patient's range of motion. If the implant selected is too small, the implant could slip out when the disc annulus is relaxed and nick an artery or the spinal cord, resulting in paralysis or death.

Improper placement of the implant can also lead to improper stress on the surrounding intervertebral bodies, which often necessitates more surgery. Placement of the implant too far anterior may cause the spine to have reduced flexion and enhanced extension. Placement of the implant too far posterior may cause the spine to have enhanced flexion and reduced extension of the spine. Both of the aforementioned scenarios are abnormal for the function of the spine and could also lead to improper loading and stressing of the entire spine.

Conventional spinal distractor devices do not provide the surgeon with the ability to accurately measure the intervertebral disc space to facilitate the proper selection, sizing and placement of the intervertebral implant (e.g., artificial disc or fusion cage).

BRIEF SUMMARY

In one aspect of this disclosure, a distractor and measuring device is disclosed that comprises a first handle operatively connected to a first paddle and a second handle operatively connected to a second paddle. The first and second handles are pivotally connected to one another such that movement of the handles relative to one another causes the paddles to move relative to each other. At least one transducer is positioned on at least one of the first and second handles for measuring an amount of force applied during distraction. A measurement rod is pivotally connected to the device and is movable in a longitudinal direction relative to the first and second paddles. A potentiometer is operatively connected to the measurement rod to measure the angular orientation of the measurement rod.

In another aspect of this disclosure, a method is disclosed for measuring an intervertebral space between two vertebrae in a patient. The method comprises inserting a distractor into the intervertebral space and measuring a force applied during distraction with at least one transducer positioned on the distractor. The intervertebral space is distracted until the measured force reaches a value corresponding to a predetermined distance an intervertebral disc annulus stretches between the vertebrae. A first longitudinal displacement of a measurement rod on the distractor is measured when the rod is moved to a position at an anterior side of an intervertebral endplate, and a second longitudinal displacement of the measurement rod on the distractor is measured when the rod is moved to a position at a posterior side of the intervertebral endplate. A length of the intervertebral endplate is calculated by taking the difference between the first and second longitudinal displacements. A first value is generated using a potentiometer on the distractor corresponding to a first angle when the measurement rod is pivoted to contact the anterior side of the endplate. A second value is generated using the potentiometer on the distractor corresponding to a second angle when the measurement rod is pivoted to contact the posterior side of the endplate. An anterior height of the intervertebral space is calculated based on the first longitudinal displacement and the first angle, and a posterior height of the intervertebral space is calculated based on the second longitudinal displacement and the second angle.

The foregoing has outlined rather generally the features and technical advantages of one or more embodiments of this disclosure in order that the following detailed description may be better understood. Additional features and advantages of this disclosure will be described hereinafter, which may form the subject of the claims of this application.

BRIEF DESCRIPTION OF THE DRAWINGS

For a more complete understanding of the present invention, reference is made to the following detailed description of an exemplary embodiment considered in conjunction with the accompanying drawings, in which.

DETAILED DESCRIPTION

A preferred spinal distractor and measuring device 10 is disclosed herein that may be used during the anterior approach to lumbar fusion or total disc replacement ("TDR"). The preferred spinal distractor and measuring device 10 utilizes sensors and a measurement rod to provide intra-operative feedback to a surgeon during spinal surgery by measuring the length of the vertebral endplate, the disc height between the anterior/posterior upper and lower vertebrae, and the magnitude of hand force applied to the device as a function of annulus distraction. This feedback allows the surgeon to quantitatively assess the amount of force applied to the distractor versus the distraction of the intervertebral disc annulus, the length of the intervertebral endplate that serves as the footprint for the implant, and the distraction of the intervertebral bodies at both anterior and posterior locations. This information will enable the surgeon to make a highly informed decision regarding the optimal size of the intervertebral implant (e.g., disc implant, fusion cage, intervertebral spacer) and the final placement of the implant for a patient undergoing a spinal fusion or TDR procedure.

FIGS. 2-5 illustrate the preferred spinal distractor and measuring device 10 in accordance with an illustrative embodiment. The spinal distractor 10 preferably includes split handles 12. The split handles 12 preferably include a pair of upper handles 12a, 12b and a pair of lower handles 12c, 12d. The upper handles 12a, 12b are preferably separated from one another to form a gap 13a and the lower handles 12c, 12d are preferably separated from one another to form a gap 13b. The gaps 13a, 13b allow for a measurement rod 14 to be operated on the device 10 without the handles 12a, 12b, 12c, 12d limiting the travel distance or movement of the measurement rod 14. This feature is especially useful when the surgeon intends to adjust the angle of the measurement rod 14 while the handles 12a, 12c and 12b, 12d are squeezed together during distraction (see FIG. 5).

The upper and lower handles 12a, 12b, 12c, 12d preferably include a hand-graspable portion 15a, 15b, 15c, 15d. The hand-graspable portions 15a, 15b, 15c, 15d are adapted to be gripped by a surgeon or user so that the upper handles 12a, 12b and lower handles 12c, 12d may be squeezed toward one another during distraction. The upper handles 12a, 12b are preferably pivotally connected to the lower handles 12c, 12d by a yoke mechanism 18 (see FIGS. 3-5).

As will be described further below, one or more sensors or transducers 11, such as (but not limited to) pressure transducer(s), force transducer(s), load cell(s), strain gauge(s), piezoelectric transducer(s) or the like, are preferably located on the hand-graspable portion 15a, 15b, 15c, 15d to measure the amount of force/pressure being applied by the surgeon or user to the upper and lower handles 12a, 12b, 12c, 12d during distraction. The sensor(s) 11 is preferably electrically connected to an amplifier circuit to produce a voltage value corresponding to the hand force/pressure applied by the surgeon during distraction, which will ultimately correspond to a displacement value for the amount of distance that the annulus ligament between the vertebrae stretches during distraction. Knowing this value will provide the surgeon with a greater understanding as to how far to distract and when to stop distraction of the vertebrae, which will avoid over distraction and under distraction, and reduce surgical complications that may require revision surgery.

Figure 3:
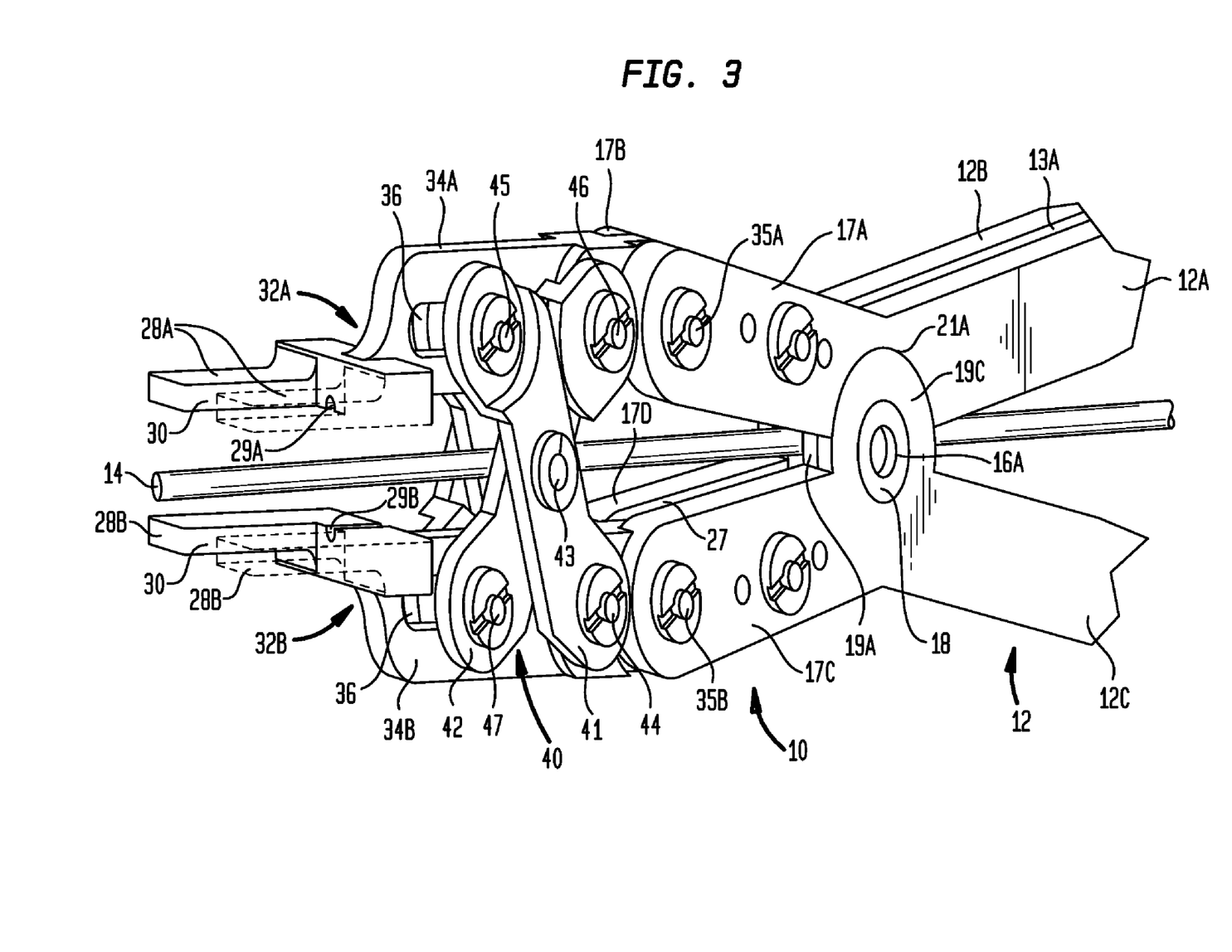
FIG. 3 is a perspective view of the front portion of the device shown in FIG. 2, the device in the open position with the potentiometer mounting bracket removed for the purpose of clarity.

Referring to FIG. 3, the upper handles 12a, 12b and lower handles 12c, 12d preferably include a semi-circular or arcuate protrusion 19a, 19b, 19c, 19d adjacent to a recessed portion 21a, 21b, 21c, 21d configured to receive and rotatably support a corresponding protrusion from an opposing handle. When assembled, protrusion 19a of upper handle 12a is located within and rotatably supported by recess portion 21c of lower handle 12c, and protrusion 19c is located within and rotatably supported by recess portion 21a of upper handle 12a. Similarly, protrusion 19b of upper handle 12b is located within and rotatably supported by recess portion 21d of lower handle 12d, and protrusion 19d is located within and rotatably supported by recess portion 21b of upper handle 12b. The yoke mechanism 18 preferably extends through an opening within the protrusions 19a, 19b, 19c, 19d to pivotally connect the upper handle 12a to the lower handle 12c and the upper handle 12b to the lower handle 12d.

A potentiometer mounting bracket 16 is preferably mounted on top of the portion of the distractor 10 that contains the yoke mechanism 18 (see FIG. 3). The bracket 16 preferably includes a fixation point for the stationary portion of a potentiometer 16a, which is preferably concentric with the yoke mechanism 18 and which allows for a rotating arm of the potentiometer to fit into the yoke mechanism 18. The purpose of this assembly is for determining the angle of the measurement rod 14, which will permit measurement of the disc height to permit a more accurate implant size selection and avoid post-operative complications.

The distractor 10 preferably includes a handle resistance mechanism 20. The handle resistance mechanism 20 includes, for example, one or more springs 22 coiled around handle adjustment bars 24. A first handle adjustment bar 24 preferably extends through an opening formed near the proximal end of the upper handle 12a and lower handle 12c. A second handle adjustment bar 24 preferably extends through an opening formed near the proximal end of the upper handle 12b and lower handle 12d. The springs 22 provide the resistance needed for smooth operation of the distractor 10 and provides sufficient resistance to prevent the surgeon from unintentionally over-distracting the annulus. A handle locking screw 26 is preferably threaded onto the ends of each handle adjustment bar 24 to allow for the surgeon to accurately pause the distraction and lock the distractor 10 into place. The ability to accurately pause the distraction permits the annulus between the vertebrae being distracted to adjust to its new position without overstretching the annulus. It is understood that other biasing means or springs may be utilized, such as, for example, leaf springs or the like.

Figure 2:
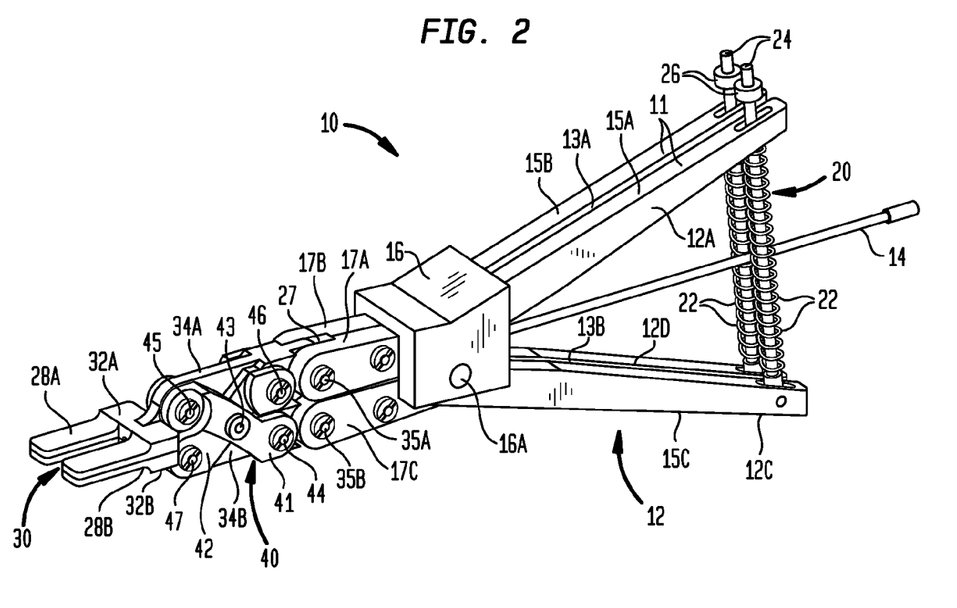
FIG. 2 is a perspective view of the device in accordance with an exemplary embodiment, the device shown in the closed position with a potentiometer mounting bracket positioned thereon.

Referring to FIGS. 2 and 3, the upper and lower handles 12a, 12b, 12c, 12d preferably terminate in a distal portion 17a, 17b, 17c, 17d. The upper handles 12a, 12b and lower handles 12c, 12d may be pinned together at their respective distal portions 17a, 17b and 17c, 17d. The ends of the distal portions 17a, 17,b, 17c, 17d are relieved so that, when assembled, a gap 27 extends between distal ends 17a, 17b and between distal ends 17c, 17d.

The distractor 10 includes an upper paddle or jaw 32a that is pivotally connected to the distal ends 17a, 17b of the upper handles 12a, 12b, and a lower paddle or jaw 32b that is pivotally connected to the distal ends 17c, 17d of the lower handles 12c, 12d. An upper connecting member 34a preferably projects from the upper paddle 32a and a lower connecting member 34b projects from the upper paddle 32b. The end of the upper connecting member 34a is located within the gap 27 between the distal ends 17a, 17b of the upper handles 12a, 12b. A pin 35a preferably pivotally connects the end of the upper connecting member 34a to the distal ends 17a, 17b of the upper handles 12a, 12b. Similarly, the end of the upper connecting member 34b is located within the gap 27 between the distal ends 17c, 17d of the lower handles 12c, 12d. A pin 35b preferably pivotally connects the end of the lower connecting member 34b to the distal ends 17c, 17d of the lower handles 12c, 12d.

The upper and lower connecting members 34a, 34b preferably include an opening or slot 36 extending therethrough. At least one cross link 40 is preferably connected to the connecting members 34a, 34b to ensure that the connecting members (and their respective paddles 32a, 32b) remain parallel to one another during operation of the device 10. It is preferred that two cross links 40 be utilized, one on each side of the connecting members 34a, 34b.

Each cross link 40 preferably includes a first link 41 that overlays a second link 42 to form a generally X-like configuration. The first and second links 41, 42 are pivotally connected to each other with a pin 43. One end of the first link 41 is preferably pivotally connected to the lower connecting member 34b via pin 44 and the opposing end of the first link 41 is slidingly connected to the upper connecting member 34a via a pin 45 that slides longitudinally within the slot 36 in the upper connecting member. Similarly, one end of the second link 42 is preferably pivotally connected to the upper connecting member 34a via pin 46 and the opposing end of the second link 42 is slidingly connected to the lower connecting member 34b via a pin 47 that slides longitudinally within the slot 36 in the lower connecting member.

The arrangement described above allows the upper and lower connecting members 34a, 34b (and their respective paddles 32a, 32b) to remain parallel to one another as they move away from one another when the upper handles 12a, 12b and lower handles 12c, 12d are squeezed toward one another by the surgeon during distraction, as shown for example in FIG. 3.

Figure 4:
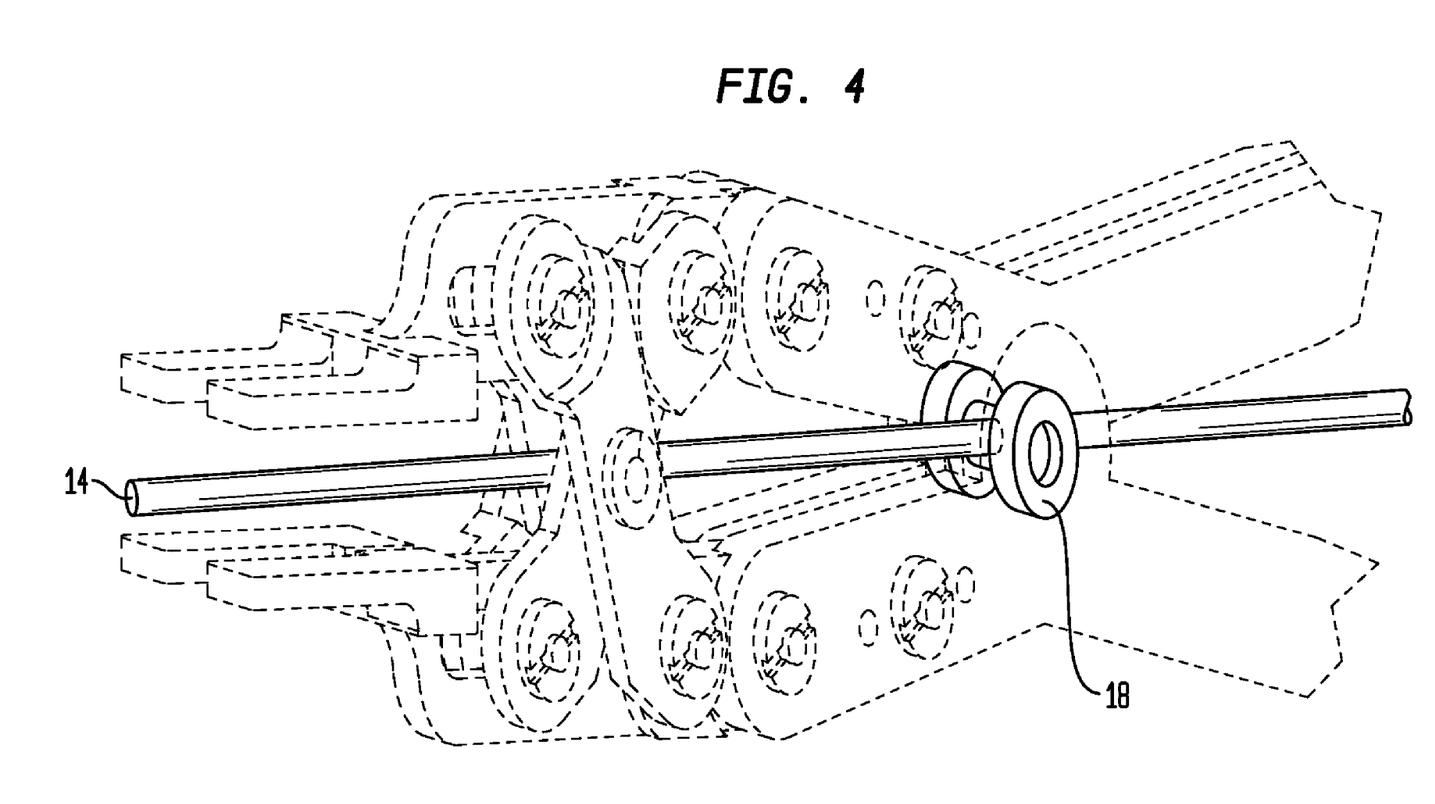
FIG. 4 is a perspective view of the front portion of the device of FIG. 3 (shown in ghost lines) with the measurement rod and yoke mechanism of the device.
Figure 5:
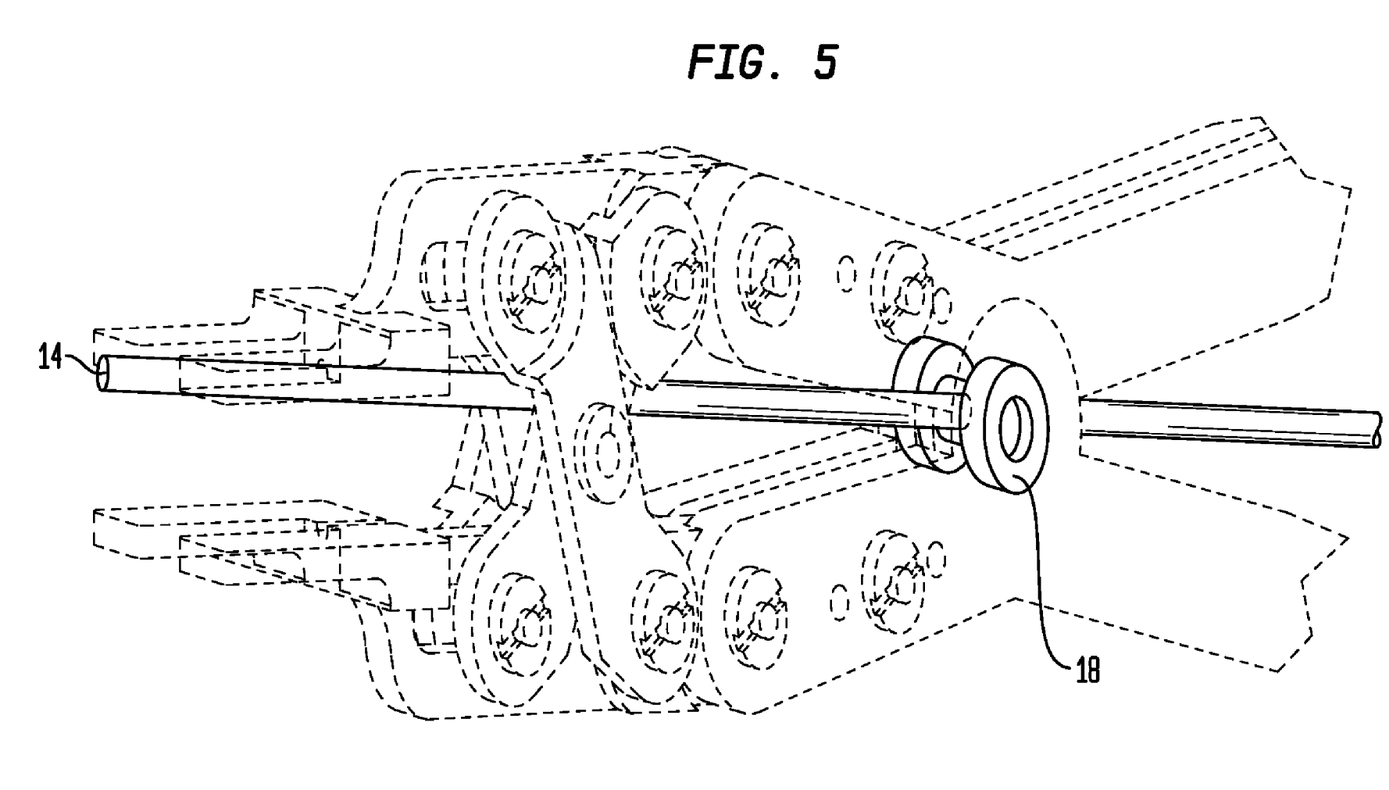
FIG. 5 illustrates the front portion of the device of FIG. 4 (shown in ghost lines) with the measurement rod and yoke mechanism pivoted upward toward the upper paddle of the device.

FIGS. 3-5 show a detailed view of the front portion of the distractor 10. The yoke 18 and measurement rod 14 provide the measuring capabilities of the distractor 10. Together, they allow for the measurement of disc height and endplate length, which will ensure a more accurate implant size selection resulting in little to no post-operative complications due to improper sizing. The measurement rod 14 is preferably marked with predefined graduations for taking length measurements in a similar fashion to a ruler and it extends through a slot or opening in the yoke 18 where the rod 14 may be slid back and forth in a longitudinal direction to measure endplate length. Alternatively, a displacement sensor, such as (but not limited to) a linear variable differential transformer (LVDT) or the like, may be utilized to produce a voltage value corresponding to the longitudinal displacement of the measurement rod 14, which would correspond to endplate length. Additionally, the yoke 18 can preferably rotate freely about the distractor 10, which allows the measurement rod 14 to be angled or pivoted up and down in the vertical direction for making disc height measurements. The disc height measurements are preferably determined by reading the potentiometer's angle and using simple geometry. Alternatively, a protractor or like device with predefined graduations may be mounted on the distractor 10 to measure the angle of the measurement rod 14.

The distractor 10 also preferably includes tapered paddle ends 28a, 28b on the upper and lower paddles 32a, 32b, each of which preferably includes a split 30 in its center. The central split 30 separates the tapered paddle end 28 so that the paddles 32a, 32b have a fork-like configuration. The tapered ends 28 allow for paddles 32a, 32b to fit easily between the discs and the split 30 in the center of each paddle end 28 allows the measurement rod 14 access to the discs for the measurement of disc height and endplate length. In other words the central split 30 allows the angle of the measurement rod 14 to be adjusted without interference from the paddles 32a, 32b (see FIG. 5).

The upper and lower paddles 32a, 32b also preferably include a semicircular recess 29a, 29b that is aligned with and opens into the central split 30. The size or radius of the semicircular recess 29a, 29b is slightly larger than that of the measurement rod 14 so that the measurement rod may be slid longitudinally through the opening formed by the semicircular recesses 29a, 29b of the device 10 when the upper and lower paddles 32a, 32b are contacting one another in their normally-closed or spring-biased position.

The distractor 10 preferably includes features such as (but not limited to) quantitative information regarding distance and distraction force. The following is a preferred description of how the distractor 10 functions during an illustrative spinal procedure.

The first step is to separate the two vertebrae that border the disc space that is being worked on. To assist the surgeon during distraction, or the separation of the vertebrae without rupture of their binding ligaments, sensor(s) 11, such as (but not limited to) one or more pressure transducers or strain gauges, located on the upper and/or lower handles 12a, 12b, 12c, 12d of the distractor 10 preferably relay the amount of pressure or force being applied by the surgeon to the handles 12 during distraction to a sensor amplifier that produces a voltage value. The voltage value corresponds to a displacement value for the amount of distance the annulus, or the fibrous tissue surrounding the disc, in between the vertebrae stretches. Knowing this value provides the surgeon with a greater understanding as to when to stop distracting.

After distraction, the measurement rod 14 is preferably extended longitudinally through the distractor 10 toward the spine. The displacement that occurs by the measurement rod 14 corresponds to the base length value of an imaginary right triangle. The rod 14 is then preferably pivoted or rotated to touch the upper and lower posterior and anterior parts of the vertebrae. In doing so, the potentiometer 16a in the distractor 10 will produce a resistance value, which is preferably converted to a voltage value by means of a Wheatstone bridge, which will preferably correspond to a certain angle on the potentiometer graphs from previous calibration experiments. This angle will, in turn, correspond to a disc height. These correlations will preferably be provided on a graph for easier access to the surgeon. Alternatively, these correlations may be computed on a computer that includes a processor and memory, and displayed for viewing by the surgeon. These features will aid in the better fit and placement of disc implant or spinal fusion cages.

The following is the test results of an "In-Lab" prototype of the spinal distractor and measuring device 10. The spinal distractor 10 measures the length of the vertebral endplate, the disc height between the anterior/posterior upper and lower vertebrae, and the magnitude of hand force applied to the device as a function of annulus distraction. To validate the design of the device 10, pressure transducers, a potentiometer, and strain gauges were calibrated to verify the spinal distractor measurements. The spinal distractor 10 was then used to evaluate intervertebral laxity following anterior lumbar discectomy to ensure the proper fit of intervertebral devices, including (but not limited to) disc implants, fusion cages, and inter-vertebral spacers.

Test Results:

1. Calibration

The first set of testing performed was to calibrate the electronic devices that were used for testing the distractor 10. These included a strain transducer, pressure transducers with load cells, and a potentiometer. From the strain transducer and pressure transducer tests the following equations were calculated to convert displacement from volts to millimeters and force from volts to Newtons:

$$\text{Force conversion } Y=3.693X-1.832 \quad (1)$$

$$\text{Displacement conversion } Y=2.46X-0.006 \quad (2)$$

Figure 6:
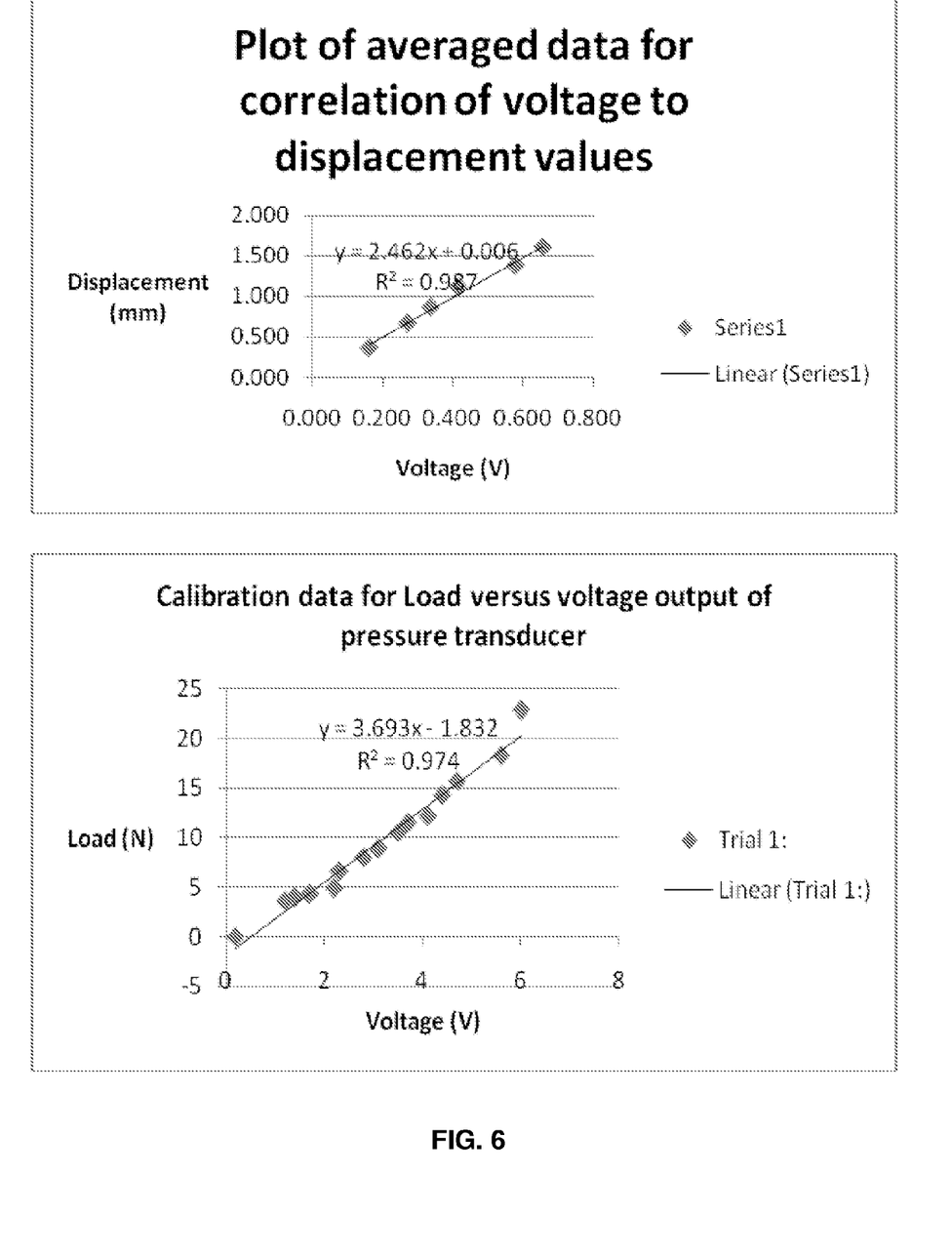
FIG. 6 depicts graphs of the linear analysis performed on a set of averages related to testing performed to calibrate electronic devices used to test a distractor.

These equations were obtained by taking the average of the trials from the strain gauge and pressure sensor calibration data. The data tables can be seen in Appendix A. The averages were graphed and a linear analysis was performed. The $R^2$ values and equations of the lines can be seen on the graphs depicted in FIG. 6.

A potentiometer was also calibrated to prepare for the second set of testing with the distractor 10. The potentiometer calibration data showed was that for an increase in one degree, the potentiometer gave an output of 0.01 volts. The data for the potentiometer calibration can be seen in Appendix A.

2. Distractor Testing

The first experiment with the distractor 10 was the hand force applied versus annulus displacement tests. The team performed nine trials, four of which were using transducer number one and five of which were using transducer number two. The data from the first four trials were thrown out due to problems with the first transducer. Therefore, trials five through nine were analyzed. However, procedural errors were discovered in trials six and nine. Appendix A shows a table that is based off of three of the five trials (Trials five, seven and eight) that were conducted with the second transducer.

Figure 7:
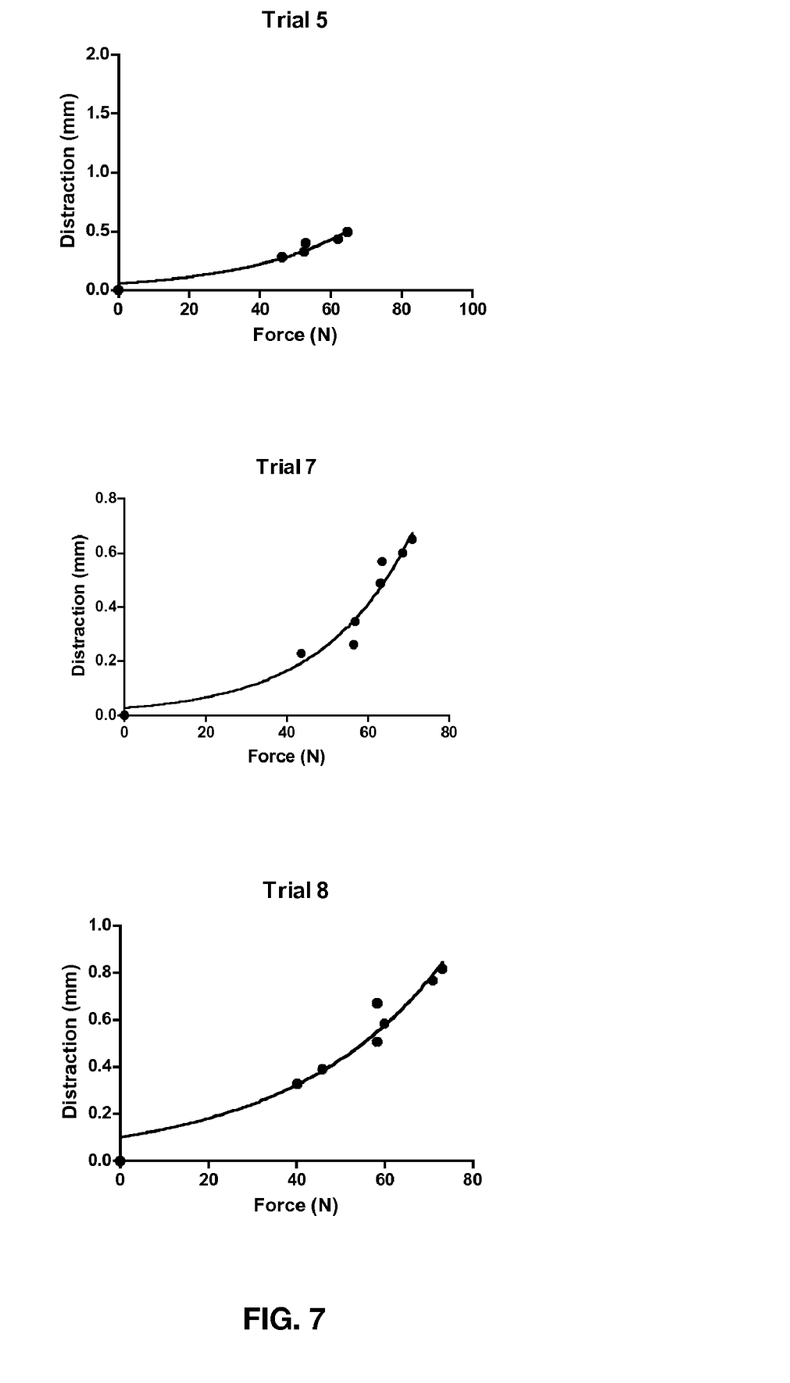
FIG. 7 depicts graphs of exponential analysis performed on data obtained during a hand force applied versus annulus distractor test.

After each trial was run, the annulus was allowed to rest before the next trial was started. This allowed the annulus to stretch so that the next trial would go further in displacement than the last. Force values were converted to Newtons and strain values were converted to displacement in millimeters using the previously mentioned equations (1) and (2), respectively. After converting the values to new units, they were zeroed out so that all trials began at zero (see Appendix A for data tables). An exponential growth analysis was performed and the data was plotted as seen in FIG. 7.

The exponential growth analysis provided k and $Y_0$ values. The value k is the rate constant, or the rate at which strain increases relative to force, and the value $Y_0$ is the displacement value when force is zero. Using the following equation for exponential growth, the force values were plotted in increments of five starting at zero and ending at one hundred for each trial.

$$\text{Exponential growth equation: } Y=Y_0 * e^{kx} \quad (3)$$

Figure 8:
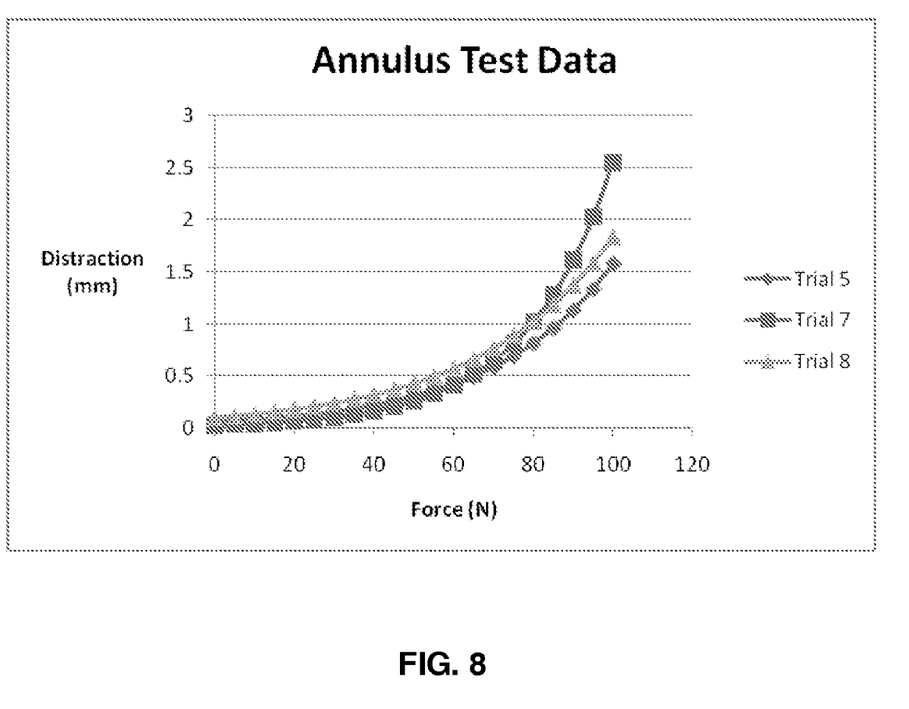
FIG. 8 depicts a graph demonstrating how the annulus is slowly stretched during distraction.

It was found that as trials of distraction increase, the force applied in Trial five, for example, 60 Newtons, stretched he ligament 0.4 mm while applying 60 Newtons in Trial eight stretched the ligament 0.6 mm. This created a pattern where the graphs for each trial stretched further and further out as the trials were run, as depicted in FIG. 8. This is symbolic of the behavior of an annulus as it is slowly stretched during distraction.

3. Disc Height and Endplate Length Testing

To calculate disc height from the results produced during testing, the following equation was used:

$$2*y*[\tan(\theta)]=\text{disc height} \quad (4)$$

This equation calculated disc height values based on the angle ($\theta$) at which the measurement or toggle bar 14 was rotated and the distance from the pivot point to the place of measurement (y). After the distractor 10 was inserted, the measurement rod or toggle bar 14 was extended to resting position, flush with the paddles 28a, 28b, and advanced to both the posterior and anterior sides of the vertebrae. The displacement that occurred was recorded for each side. This stood for the "y" value for the imaginary triangle used in the calculation of disc height. Next, the measurement rod or toggle bar 14 was toggled or pivoted to touch the top part of the vertebrae. The movement of the potentiometer shaft produced a voltage output that was correlated to an angle value. Then, disc height was calculated using equation (4) above.

Having described and illustrated the principles of this application by reference to one or more preferred embodiments, it should be apparent that the preferred embodiment(s) may be modified in arrangement and detail without departing from the principles disclosed herein and that it is intended that the application be construed as including all such modifications and variations insofar as they come within the spirit and scope of the subject matter disclosed herein.

APPENDIX A

Data Tables

1. Transducer Calibration

| Trials | |
|---|---|
| Actual Displacement (mm) | Voltage (V) |
| 1 | |
| 0.410 | 0.168 |
| 0.630 | 0.237 |
| 0.810 | 0.298 |

-continued

Trials

| Actual Displacement (mm) | Voltage (V) |
|---|---|
| 1.020 | 0.347 |
| 1.300 | 0.480 |
| 1.490 | 0.555 |
| 2 | |
| 0.370 | 0.253 |
| 0.630 | 0.353 |
| 0.870 | 0.430 |
| 1.130 | 0.497 |
| 1.460 | 0.676 |
| 1.730 | 0.756 |
| 3 | |
| 0.300 | 0.066 |
| 0.740 | 0.225 |
| 0.920 | 0.284 |
| 1.200 | 0.404 |
| Average | |
| 0.360 | 0.162 |
| 0.667 | 0.272 |
| 0.867 | 0.337 |
| 1.117 | 0.416 |
| 1.380 | 0.578 |
| 1.610 | 0.656 |

2. Load Cell/Pressure Transducer Calibration

| Load Cell Calibration: Load (N) | Voltage (V) |
|---|---|
| 0 | 0.19 |
| 3.6 | 1.2 |
| 4 | 1.4 |
| 4.3 | 1.7 |
| 4.9 | 2.2 |
| 6.6 | 2.3 |
| 8 | 2.8 |
| 8.9 | 3.1 |
| 10.5 | 3.5 |
| 11.5 | 3.7 |
| 12.2 | 4.1 |
| 14.3 | 4.4 |
| 15.7 | 4.7 |
| 18.3 | 5.6 |
| 22.9 | 6 |

3. Potentiometer Calibration Data

| Voltage | Degree |
|---|---|
| Trial 1 | |
| −0.06 | 45 |
| −0.115 | 50 |
| −0.15 | 55 |
| −0.21 | 60 |
| −0.27 | 65 |
| −0.31 | 70 |
| −0.38 | 75 |
| −0.42 | 80 |
| −0.5 | 85 |
| −0.56 | 90 |
| Trial 2: | |
| −0.05 | 45 |
| −0.11 | 50 |
| −0.16 | 55 |
| −0.21 | 60 |
| −0.26 | 65 |
| −0.33 | 70 |
| −0.38 | 75 |
| −0.42 | 80 |
| −0.49 | 85 |
| −0.56 | 90 |
| Trial 3: | |
| −0.06 | 45 |
| −0.1 | 50 |
| −0.15 | 55 |
| −0.2 | 60 |
| −0.25 | 65 |
| −0.29 | 70 |
| −0.34 | 75 |
| −0.41 | 80 |
| −0.47 | 85 |
| −0.54 | 90 |
| Trial 4: | |
| −0.05 | 45 |
| −0.09 | 50 |
| −0.145 | 55 |
| −0.19 | 60 |
| −0.25 | 65 |
| −0.3 | 70 |
| −0.35 | 75 |
| −0.42 | 80 |
| −0.48 | 85 |
| −0.54 | 90 |

4. Force Applied to Annulus Distraction Testing Data

| Pressure (volts) | Strain (volts) | Force (N) | Distraction (mm) |
|---|---|---|---|
| Trial 5 | | | |
| 1.6 | 0.019 | 0 | 0 |
| 14.1 | 0.132 | 46.1625 | 0.27798 |
| 15.8 | 0.153 | 52.4406 | 0.32964 |
| 15.9 | 0.181 | 52.8099 | 0.39852 |
| 18.4 | 0.195 | 62.0424 | 0.43296 |
| 19.1 | 0.22 | 64.6275 | 0.49446 |
| Trial 7 | | | |
| 1.8 | 0.031 | 0 | 0 |
| 13.6 | 0.124 | 43.5774 | 0.22878 |
| 17.1 | 0.137 | 56.5029 | 0.26076 |
| 17.2 | 0.172 | 56.8722 | 0.34686 |
| 18.9 | 0.229 | 63.1503 | 0.48708 |
| 19 | 0.262 | 63.5196 | 0.56826 |
| 20.4 | 0.275 | 68.6898 | 0.60024 |
| 21 | 0.296 | 70.9056 | 0.6519 |
| Trial 8 | | | |
| 1.7 | 0.032 | 0 | 0 |
| 12.6 | 0.165 | 40.2537 | 0.32718 |
| 14.1 | 0.19 | 45.7932 | 0.38868 |
| 17.5 | 0.238 | 58.3494 | 0.50676 |
| 17.9 | 0.269 | 59.8266 | 0.58302 |
| 17.5 | 0.304 | 58.3494 | 0.66912 |
| 20.9 | 0.344 | 70.9056 | 0.76752 |
| 21.5 | 0.364 | 73.1214 | 0.81672 |

5. Exponential Growth Equation Data

| Trial 5 | | Trial 7 | | Trial 8 | |
|---|---|---|---|---|---|
| $Y0 = 0.05815$ Force | $k = 0.03$ $Y = Y0*e^{kx}$ | $Y0 = 0.02639$ Force | $k = 0.0457$ $Y = Y0*e^{kx}$ | $Y0 = 0.1012$ Force | $k = 0.02899$ $Y = Y0*e^{kx}$ |
| 0 | 0.05815 | 0 | 0.02639 | 0 | 0.1012 |
| 5 | 0.068582 | 5 | 0.033166 | 5 | 0.116985 |
| 10 | 0.080885 | 10 | 0.041683 | 10 | 0.135233 |
| 15 | 0.095395 | 15 | 0.052386 | 15 | 0.156327 |
| 20 | 0.112508 | 20 | 0.065837 | 20 | 0.180711 |
| 25 | 0.132691 | 25 | 0.082743 | 25 | 0.208899 |
| 30 | 0.156495 | 30 | 0.103989 | 30 | 0.241483 |
| 35 | 0.184569 | 35 | 0.130691 | 35 | 0.27915 |
| 40 | 0.21768 | 40 | 0.164249 | 40 | 0.322692 |
| 45 | 0.25673 | 45 | 0.206425 | 45 | 0.373026 |
| 50 | 0.302786 | 50 | 0.25943 | 50 | 0.431212 |
| 55 | 0.357104 | 55 | 0.326045 | 55 | 0.498473 |
| 60 | 0.421166 | 60 | 0.409766 | 60 | 0.576225 |
| 65 | 0.49672 | 65 | 0.514984 | 65 | 0.666106 |
| 70 | 0.585828 | 70 | 0.647219 | 70 | 0.770006 |
| 75 | 0.690921 | 75 | 0.81341 | 75 | 0.890113 |
| 80 | 0.814868 | 80 | 1.022274 | 80 | 1.028955 |
| 85 | 0.961049 | 85 | 1.28477 | 85 | 1.189453 |
| 90 | 1.133455 | 90 | 1.614669 | 90 | 1.374986 |
| 95 | 1.336789 | 95 | 2.029278 | 95 | 1.589459 |
| 100 | 1.5766 | 100 | 2.550348 | 100 | 1.837385 |

What is claimed is:

1. A distractor and measuring device, comprising: a first handle operatively connected to a first paddle and a second handle operatively connected to a second paddle, the first and second handles being pivotally connected to one another such that movement of the handles relative to one another causes the paddles to move relative to each other; at least one transducer positioned on at least one of the first and second handles for measuring an amount of force applied during distraction; a measurement rod pivotally connected to the device and movable in a longitudinal direction relative to the first and second paddles; a potentiometer operatively connected to the measurement rod to measure the angular orientation of the measurement rod; and a yoke mechanism pivotally connecting the first handle to the second handle, the yoke mechanism having an opening through which the measurement rod passes to permit movement of the measurement rod in the longitudinal direction, and the yoke mechanism being able to turn at least partially relative to the first and second handles so that the measurement rod may be pivoted to adjust the angular orientation of the measurement rod.

2. The distractor and measuring device according to claim 1, wherein the at least one transducer is selected from the group consisting of a pressure transducer, force transducer, load cell, strain gauge, and piezoelectric transducer.

3. The distractor and measuring device according to claim 1, further comprising:
a third handle spaced apart from the first handle and operatively connected to the first paddle; and
a fourth handle spaced apart from the second handle and operatively connected to the second paddle, the second and fourth handles being pivotally connected to first and third handles such that movement of the first and third handles relative to second and fourth handles causes the paddles to move relative to each other,
wherein the spacing between the first and third handles and between the second and fourth handles permits the angular orientation of the measurement rod to be adjusted without restriction from the handles.

4. The distractor and measuring device according to claim 3, further comprising at least one transducer positioned on at least one of the third and fourth handles for measuring an amount of force applied during distraction.

5. The distractor and measuring device according to claim 4, wherein the at least one transducer is selected from the group consisting of a pressure transducer, force transducer, load cell, strain gauge, and piezoelectric transducer.

6. The distractor and measuring device according to claim 1, further comprising a spring to bias the handles in a direction where the paddles move toward one another to a closed position.

7. The distractor and measuring device according to claim 6, further comprising:
a handle adjustment bar operatively connected to the second handle and having a free end that extends through an opening in the first handle; and
an adjustable locking screw threaded onto the free end of the handle adjustment bar to maintain the position of the first handle relative to the second handle during distraction and prevent the spring from biasing the handles to the closed position.

8. The distractor and measuring device according to claim 1, wherein the first paddle and the second paddle are each split at least partially in the longitudinal direction so that the measurement rod may extend through the split when the angular orientation of the measurement rod is adjusted.

9. The distractor and measuring device according to claim 8, wherein the first and second paddles include an arcuate recess that defines an opening through which the measurement rod may pass to permit movement of the measurement rod in the longitudinal direction when the first and second paddles engage one another in a closed position.

10. The distractor and measuring device according to claim 1, further comprising:
a first connecting member extending from the first paddle and pivotally connected to a distal end of the second handle, the first connecting member including an opening;

a second connecting member extending from the second paddle and pivotally connected to a distal end of the first handle, the second connecting member including an opening; and a cross link assembly operatively connected to the first and second connecting members to keep the paddles parallel to one another during distraction.

11. The distractor and measuring device according to claim 10, wherein the cross link assembly comprises:

a first link pivotally connected to a second link, a proximal end of the first link pivotally connected to a distal end of the second handle and a proximal end of the second link pivotally connected to a distal end of the first handle;

a first pin extending from a distal end of the first link, the first pin dimensioned to slide longitudinally within the opening in the first connecting member; and a second pin extending from a distal end of the second link, the second pin dimensioned to slide longitudinally within the opening in the second connecting member.

12. The distractor and measuring device according to claim 11, further comprising a second cross link assembly operatively connected to the first and second connecting members to keep the paddles parallel to one another during distraction.

13. The distractor and measuring device according to claim 1, wherein a plurality of graduations are provided on the measurement rod to determine the longitudinal displacement of the measurement rod.

14. The distractor and measuring device according to claim 1, further comprising a displacement sensor to determine the longitudinal displacement of the measurement rod.

15. A distractor and measuring device, comprising: a first handle operatively connected to a first paddle and a second handle operatively connected to a second paddle, the first and second handles being pivotally connected to one another such that movement of the handles relative to one another causes the paddles to move relative to each other; means for measuring an amount of force applied during distraction; a measurement rod pivotally connected to the device and movable in a longitudinal direction relative to the first and second paddles; means for measuring the angular orientation of the measurement rod; and a yoke mechanism pivotally connecting the first handle to the second handle, the yoke mechanism having an opening through which the measurement rod passes to permit movement of the measurement rod in the longitudinal direction, and the yoke mechanism being able to turn at least partially relative to the first and second handles so that the measurement rod may be pivoted to adjust the angular orientation of the measurement rod.

16. The distractor and measuring device according to claim 15, wherein the means for measuring an amount of force applied during distraction comprises at least one transducer positioned on at least one of the first and second handles for measuring an amount of force applied during distraction.

17. The distractor and measuring device according to claim 15, wherein the means for measuring the angular orientation of the measurement rod comprises a potentiometer operatively connected to the measurement rod.

18. The distractor and measuring device according to claim 15, further comprising:

a third handle spaced apart from the first handle and operatively connected to the first paddle; and a fourth handle spaced apart from the second handle and operatively connected to the second paddle, the second and fourth handles being pivotally connected to first and third handles such that movement of the first and third handles relative to second and fourth handles causes the paddles to move relative to each other, wherein the spacing between the first and third handles and between the second and fourth handles permits the angular orientation of the measurement rod to be adjusted without restriction from the handles.

19. The distractor and measuring device according to claim 15, further comprising:

a spring for biasing the handles in a direction where the paddles move toward one another to a closed position;

a handle adjustment bar operatively connected to the second handle and having a free end that extends through an opening in the first handle; and an adjustable locking screw threaded onto the free end of the handle adjustment bar to maintain the position of the first handle relative to the second handle during distraction.

20. The distractor and measuring device according to claim 15, wherein the first paddle and the second paddle are each split at least partially in the longitudinal direction so that the measurement rod may extend through the split when the angular orientation of the measurement rod is adjusted.

21. The distractor and measuring device according to claim 20, wherein the first and second paddles include an arcuate recess that defines an opening through which the measurement rod may pass to permit movement of the measurement rod in the longitudinal direction when the first and second paddles engage one another in a closed position.

22. The distractor and measuring device according to claim 15, further comprising means for keeping the paddles parallel to one another during distraction.

23. The distractor and measuring device according to claim 15, further comprising means for determining the longitudinal displacement of the measurement rod.

* * * * *